United States Patent [19]

Frueh

[11] Patent Number: 4,859,608
[45] Date of Patent: Aug. 22, 1989

[54] METHOD AND APPARATUS FOR TITRIMETRIC CONTENT DETERMINATION IN A CHEMICAL SOLUTION

[75] Inventor: Peter Frueh, Zurich, Switzerland

[73] Assignee: Mettler Instrumente AG, Greifensee, Switzerland

[21] Appl. No.: 90,895

[22] Filed: Aug. 31, 1987

Related U.S. Application Data

[63] Continuation of Ser. No. 804,838, Dec. 4, 1985, abandoned.

[30] Foreign Application Priority Data

Jan. 18, 1985 [CH] Switzerland ............................ 224/85

[51] Int. Cl.⁴ ...................... G01N 31/16; G01N 31/22
[52] U.S. Cl. ..................................... 436/163; 436/164; 422/75; 422/76; 422/77
[58] Field of Search ........................ 436/163, 164, 166; 422/75, 76, 77

[56] References Cited

PUBLICATIONS

Websters Third New Inter. Dictionary, Merriam Webster Inc., Massachusetts, 1986, p. 1707.
Schweid, N., "On Line Titrumetry", ISA, vol. 19, 1981, Conference Proceedings, 27th Annual ISA Anal. Inst. Sym., K. C. Mo, 3/1981.

Primary Examiner—David L. Lacey
Assistant Examiner—L. Johnson
Attorney, Agent, or Firm—Laubscher & Laubscher

[57] ABSTRACT

In a new method for the titrimetric determination of the contents in a chemical solution, wherein a quantity of a reaction component, corresponding in each case to the change of a certain physical-chemical magnitude or a value derived from that, is added to a reaction component and this added quantity is so regulated that it will be a function of the prior and/or predetermined magnitude change or changes and the already added total quantity of one of the reaction components. In the method mentioned, the minimum quantity added is not allowed to fall below a predetermined percentage, e.g., 1.0 percent, or even 0.5 to 0.1 percent, of the already added quantity. The apparatus for performing the method therefore contains devices operable to regulate the quantity to be added as a function of the magnitude change and the already added total quantity of one of the reaction components. Potentiometric titration is the most important area of application of the new determination method.

13 Claims, 3 Drawing Sheets

METHOD AND APPARATUS FOR TITRIMETRIC CONTENT DETERMINATION IN A CHEMICAL SOLUTION

CROSS-REFERENCE TO RELATED APPLICATION

This application is a continuation of parent application Ser. No. 804,838 filed Dec. 4, 1985, (now abandoned).

FIELD OF THE INVENTION

The invention described herein relates to a method for the titrimetric determination of the contents of components in chemical solutions. The principal field of application of this method consists of potentiometric, colorimetric, and coulometric titrations. Potentiometric determination methods are based on the determination of pH, ion activity, redox, and other chemical potentials.

BRIEF DESCRIPTION OF THE PRIOR ART

Prior methods of this kind take place through the maintenance of constant volume steps, whereby the potentiometric determination serves merely to control or monitor the attainment or exceeding of the one or more points of equivalence. The volume of the particular titration medium to be added periodically can usually be adjusted at the start of the determination process. The accuracies and reproducibilities of the results that can be achieved with such methods naturally are limited.

The introduction of reaction components as a function of previously adjustable potential differences makes it possible to achieve clearly improved result accuracies.

From the US-PS No. 4,058,365 and DE-OS No. 2,617,346 a method for automatic titration is known in which the dosing of the added medium is permanently adjusted to the course of the titration curve by means of digital control. The titration is started with at least one dosage of a preselected size, each dosage of titrant, i.e. the added medium, thereafter and throughout the total course of the titration being precalculated and controlled on the basis of transducer signal change per added titrant volume unit at the preceding medium to be added is calculated in advance on the basis of the change of the measurement magnitude transformer signal $\Delta S$ per volume unit added $\Delta V$. However, according to this known method the calculations may become uncertain if the minimum value of the individual dosages should be too small. Therefore, a sufficient accuracy of the determinations cannot be attained as required in the practice and the titration will be time consuming.

S. Ebel and B. Reyer, "Dynamic Control of Volume Increments", Fresenius Z. Analytische Chemie, 1982, Vol. 312, pages 346-351, suggest for the control algorithms of potentiometric titrations to determine in advance an (absolute) minimal or maximal reagent addition, and to add the individual titration medium dosings in portions while allow the adjustment and while determining the potential between the portions. Thus, constant potential steps are achieved, but at the expense of the determination time.

Accordingly, the present invention was developed to provide a method for the titrimetric determination of contents of components in chemical solutions, where one can determine or achieve both a desired determination accuracy and a practical determination time. It must be pointed out here that both of the characteristics mentioned are of great practical importance in any commercial or industrial employment of this method.

SUMMARY OF THE INVENTION

A primary object of the present invention is to provide a method for the titrimetric determination of the contents in a chemical reaction system, wherein certain quantities of a reaction component which is capable of reacting with the said at least one component are added repeatedly to a chemical solution containing the least one component, or are generated in the reaction system, and wherein the change of a certain physicochemical value in the reaction system is controlled, such as by measuring it, as a result from a reaction of the reaction component with the said at least one component in the chemical solution. The added quantity of the reaction component corresponds with the change of the physicochemical value, i.e. the measured signal, which results from an immediately preceding and/or predetermined added quantity of reaction component or a value derived from that. The mentioned quantity to be added in each case furthermore is so determined that it will be a function of the already added total quantity of one of the reaction components.

According to a more specific object of the invention, the quantities to be added cannot fall below a given amount—for example 1.0 percent or 0.5 or 0.1 percent—of the total quantity already added of one of the reaction components.

According to a further object of the invention, apparatus is provided for performing the aforementioned method, including in addition to the usual and necessary structural parts—such as containers, conduits, conveying, measuring, control and regulating equipment—additional means for facilitating regulation of the particular quantity of the reaction component to be added in accordance with the changes of a physicochemical magnitude that are to be controlled in the reaction system, or in accordance with a value derived herefrom, as well as means for regulating the particular quantity to be added as a function of the total quantity already added to one of the reaction components.

The apparatus in a practical manner contains means operable to limit the particular quantity to be added preferably to a minimum of a given amount, such as 1.0 percent, or possibly as low as a minimum of 0.5 or 0.1 percent, of the already added total quantity of one of the reaction components. The aforementioned means for the regulation of the particular quantity to be added are either predetermined or they are such that, at the start of each determination, they will permit the input of the parameters necessary for this.

The method according to the invention is employed mainly to perform potentiometric titrations, that is to say, titrations based on the potentiometric measurement of pH values, ion potentials, or redox potentials; one can however also perform colorimetric and coulometric titrations with this.

BRIEF DESCRIPTION OF THE DRAWINGS

Other objects and advantages of the invention will become apparent from a study of the following specification when viewed in the light of the accompanying drawings, in which.

DETAILED DESCRIPTION

The method according to the invention and the corresponding device will now be explained in greater detail with the help of a practical application example. The device, by means of which the following titration is performed, is a complete analysis station for titrimetric analysis. It facilitates the automatic performance of a titration, including evaluation. The analysis result is calculated in the desired unit with the inclusion of the sample weight.

Figure 1:
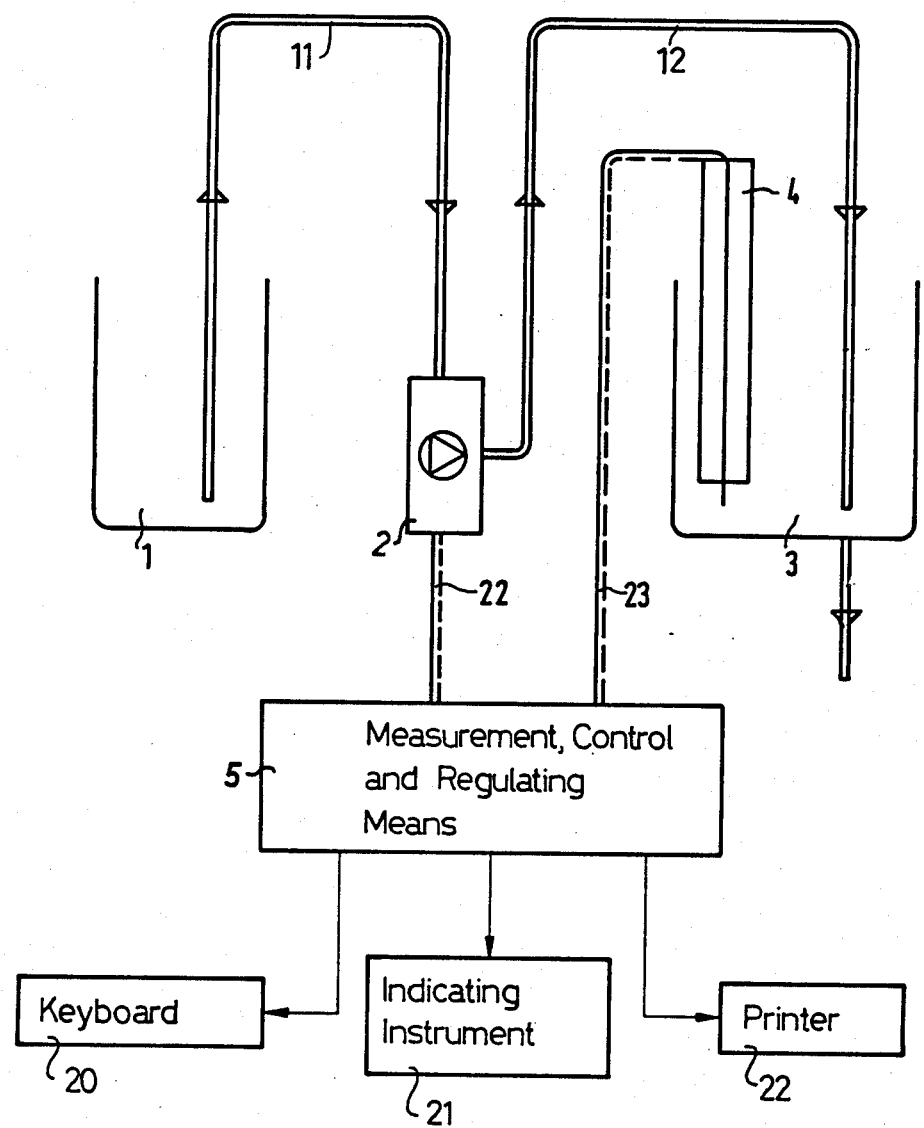
FIG. 1 is a diagrammatic illustration of one form of a titration system in accordance with the present invention.

Referring now to FIG. 1, the particular quantity of the titrant to be added is supplied from storage container 1 to receptacle 3 by automatic burette means including conveying means 2 and conduits 11 and 12, which receptacle 3 contains the sample solution the components of which are to be determined. The change of the determined physical-chemical magnitude takes place by means of the measurement probe 4 in the reaction system mentioned. Both the burette and the measurement probe are connected via lines 22 and 23, respectively, with the measurement, control, and regulating instrument 5 which contains the hardware and software necessary for the performance and regulation of the titration described here. Instrument 5 includes a keyboard 20 for inputting data or parameters, and it also contains an indication instrument 21 and, if necessary, a printer 22.

To perform a titration procedure, it is first of all necessary to input the sample weight and the sample identification number. Everything else is done automatically. The scale and the printer can be directly connected for result recording. Special aid functions facilitate the likewise reliable determination of the titration agent concentration (factor determination) as well as the blank determination necessary for certain analyses.

In addition to the possibility of the parameter input corresponding with the concentration of the reaction component in the added solution, with the (initial) dosage volume, and with various titration and evaluation methods, the titration, apparatus employed here also includes means for adjusting the minimum increment as a function of the already dosed volume. In the following titrations, that volume represents one of the most important configuration parameters.

The relevant data for implementation by way of example are as follows:

Titration of sulfanilic acid with sodium nitrite.
Sample: sulfanilic acid
Preparation: 0.1 g sulfanilic acid, 60 ml 0.5 n HBr
Calcuation constant: % Mw/10 = 17.319
(Mw = molecular weight)
Indication: Dm 140
Titration agent: Sodium nitrite 0.1 n a 10 ml-burette.
The titration took place:
(1) According to the state of the art, in our case here with configuration parameter (1) equal to 102, and
(2) According to the invention, that is to say, with configuration parameter (1) equal to 2.

Figure 2:
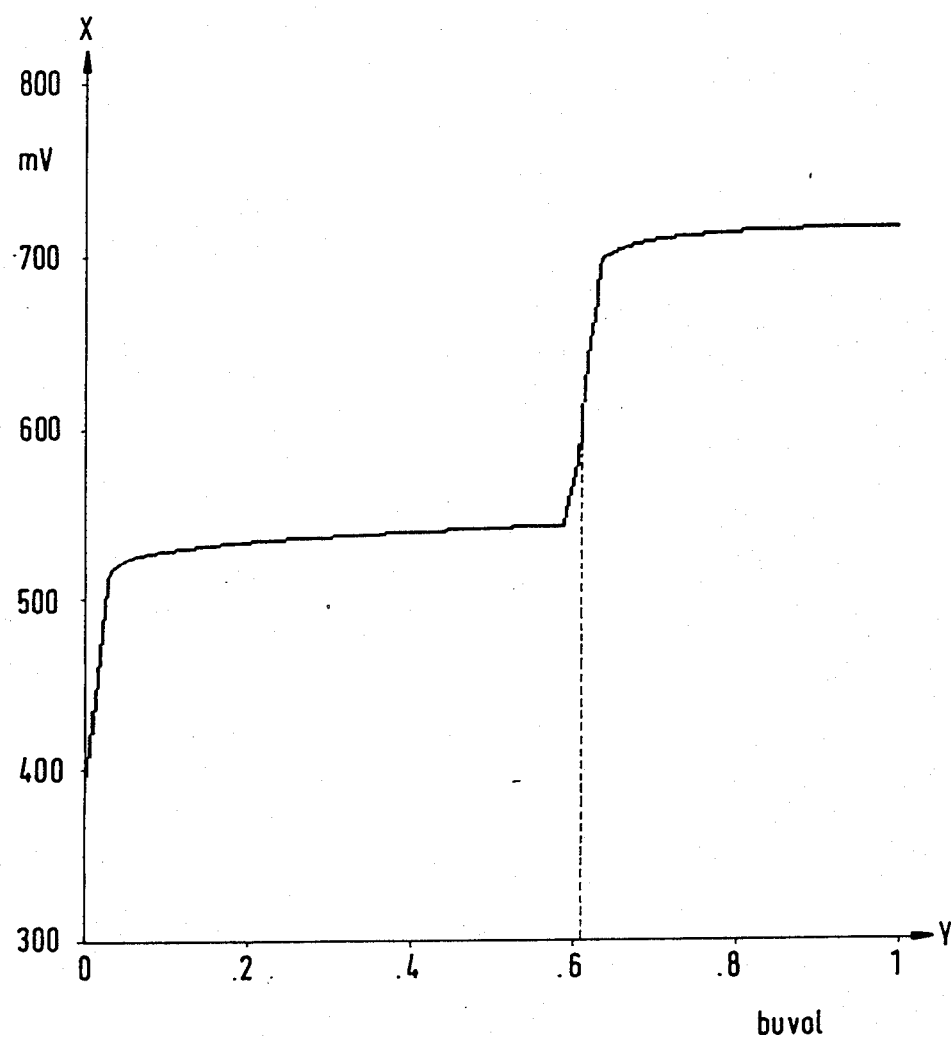
FIG. 2 is a graph illustrating a titration process according to the prior art, illustrating the electrical signal (in mV) plotted against the burette volume.

First Titration (FIG. 2)

Concentration determination, value table
Weighed sample: g 0.1024
Start signal (mV): 394.7

TABLE 1

| Increment buvol | Signal Change mV |
|---|---|
| .02850 | 121.7 |
| .01450 | 5.0 |
| .00750 | 1.8 |
| .01450 | 2.0 |
| .02000 | 2.1 |
| .02000 | 1.4 |
| .02000 | 1.2 |
| .02000 | 1.0 |
| .02000 | 1.0 |
| .02000 | .8 |
| .02000 | .8 |
| .02000 | .7 |
| .02000 | .7 |
| .02000 | .6 |
| .02000 | .5 |
| .02000 | .6 |
| .02000 | .5 |
| .02000 | .5 |
| .02000 | .4 |
| .02000 | .5 |
| .02000 | .4 |
| .02000 | .3 |
| .02000 | .4 |
| .02000 | .4 |
| .02000 | .4 |
| .02000 | .4 |
| .02000 | .4 |
| .02000 | .4 |
| .02000 | .5 |
| .02000 | .5 |
| .02000 | 37.6 |
| .00400 | 31.4 |
| .00100 | 5.7 |
| .00200 | 10.6 |
| .00100 | 5.4 |
| .00150 | 6.7 |
| .00250 | 8.2 |
| .00350 | 9.4 |
| .00350 | 7.2 |
| .00550 | 26.8 |
| .00100 | 3.6 |
| .00200 | 1.4 |
| .00100 | .9 |
| .00250 | 1.3 |
| .00500 | 1.9 |
| .01000 | 2.3 |
| .01950 | 3.0 |
| .02000 | 2.0 |
| .02000 | 1.4 |
| .02000 | 1.1 |
| .02000 | .9 |
| .02000 | .7 |
| .02000 | .6 |
| .02000 | .6 |
| .02000 | .4 |
| .02000 | .4 |
| .02000 | .4 |
| .02000 | .3 |
| .02000 | .2 |
| .02000 | .2 |
| .02000 | .2 |
| .02000 | .3 |
| .02000 | .1 |
| .00950 | .1 |

Equivalence Volume: 0.6071 buvol

The titration according to the prior state of the art thus, in 64 titration steps, supplied a total volume of titration agent at the equivalence point amounting to 0.60716 burette volume (for 0.1024 g of sampled weighed in). This titration took 23 minutes.

The values from the above Table 1 are illustrated in FIG. 2, wherein the x-axis shows the burette volume (in parts) and the y-axis shows the signal (in mV).

Figure 3:
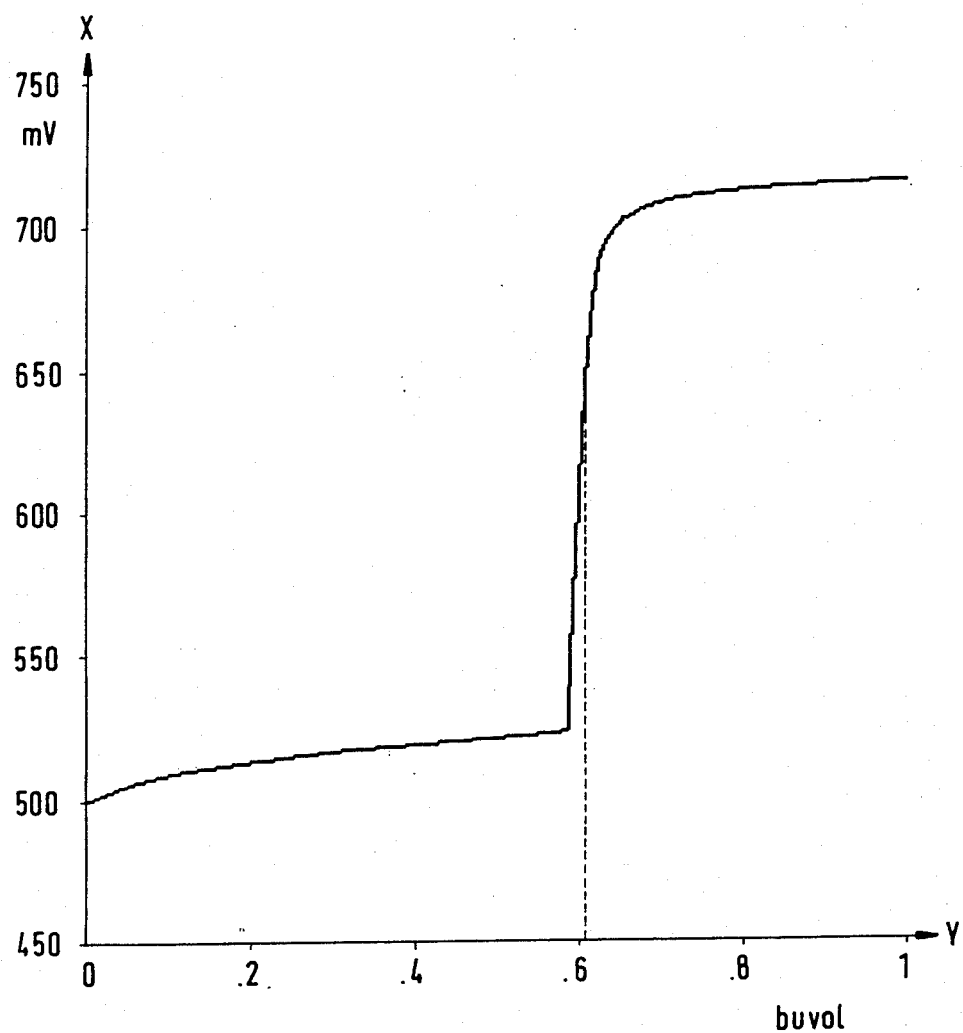
FIG. 3 is a graph illustrating a titration process performed in accordance with the present invention.

Second Titration (FIG. 3)

Concentration determination, value table
Sample weighed: g, 0.1028
Starting signal (mV): 498.5

TABLE 2

| Increment buvol | Signal Change mV |
| --- | --- |
| .02850 | 3.6 |
| .01450 | 1.6 |
| .00750 | .8 |
| .01450 | 1.2 |
| .02000 | 1.4 |
| .02000 | 1.1 |
| .02000 | 1.2 |
| .02000 | .9 |
| .02000 | .8 |
| .02000 | .8 |
| .02000 | .8 |
| .02000 | .7 |
| .02000 | .7 |
| .02000 | .7 |
| .02000 | .6 |
| .02000 | .7 |
| .02000 | .5 |
| .02000 | .4 |
| .02000 | .5 |
| .02000 | .4 |
| .02000 | .4 |
| .02000 | .5 |
| .02000 | .4 |
| .02000 | .5 |
| .02000 | .6 |
| .02000 | .7 |
| .02000 | 123.8 |
| .00600 | 20.4 |
| .00600 | 14.7 |
| .00600 | 9.0 |
| .01250 | 6.4 |
| .00650 | 2.4 |
| .01250 | 3.1 |
| .02000 | 3.1 |
| .02000 | 1.8 |
| .02000 | 1.4 |
| .02000 | .7 |
| .02000 | .7 |
| .02000 | .6 |
| .02000 | .6 |
| .02000 | .6 |
| .02000 | .3 |
| .02000 | .4 |
| .02000 | .3 |
| .02000 | .3 |
| .02000 | .3 |
| .02000 | .3 |
| .02000 | .2 |
| .02000 | .2 |
| .22000 | .1 |
| .00550 | .1 |

Equivalence volume: 0.60414 buvol

Here the results are as follows:

Total volume of titration agent at the equivalence point: 0.60414 burette volume (for 0.1028 g sample weighed); the deviation compared to the first operation thus can be neglected.

On the other hand, this titration took only 15 minutes and 20 seconds and the number of titration steps was only 51. The smallest increment in this case likewise is 0.006 buvol, in contrast to the first titration, where the same magnitude drops to 0.001.

In this case, the table values are illustrated in FIG. 3 (same coordinate designation as in FIG. 2).

The example illustrated clearly shows one great advantage of the invention. By means of the suitable choice of the minimum increment to be dosed in, with moderate requirements for measurement accuracy, the titration time (especially in the equivalence range) can be definitely reduced. The choice of the minimum increment can vary considerably, according to the requirements regarding time consumption and accuracy in each specific case.

What is claimed is:

1. A method for the titrimetric determination of the content of at least one given component in the chemical solution capable of reacting with at least one reaction component comprising the steps of:
   (a) successively providing in a chemical solution quantities of at least one reaction component, starting with one reaction component, starting with one initial preselected quantity of said at least one reaction component;
   (b) measuring the change of a certain physico-chemical value which results from the reaction of each said reaction component quantity with said one given component;
   (c) determining the next successively provided quantity of said reaction component as a function of said change of said physicochemical value resulting from an immediately preceding provided quantity of said reaction component;
   (d) determining the total of the previously successively provided quantities of said reaction component including said immediate preceding quantity;
   (e) determining said next reaction component quantity as a percentage relative to the total of the previously provided reaction component quantities; and
   (f) providing in said solution the greater of:
      (1) said determined next quantity of step (c), or
      (2) an amount of not less than 0.1 per cent of the total of the previously provided quantities of the reaction component.

2. A method as defined in claim 1, wherein the next quantity to be provided is an amount of not less than 0.5 percent of the total of the previously provided quantities of said reaction component.

3. A method as defined in claim 1, wherein in the next quantity to be provided is an amount of not less than 1 percent of the total of the previously provided quantities of the component.

4. A potentiometric titration method, including titrations based on the potentiometric measurement of pH-values, ion potentials, or redox potentials, for determining the content of at least one given component in a chemical solution capable of reacting with at least one reaction component, capable of reacting with at least one reaction component, comprising the steps of:
   (a) successively providing in a chemical solution quantities of at least one reaction component, starting with one initial preselected quantity of said at least one reaction component;
   (b) measuring the change of a certain physicochemical value which results from the reaction of each said reaction component quantity with said one given component;
   (c) determining the next successively provided quantity of said reaction component as a function of said change of said physicochemical value resulting from an immediately preceding provided quantity of said reaction component;

(d) determining the total of the previously successively provided quantities of said reaction component including said immediately preceding quantity;

(e) determining said next reaction component quantity as a percentage relative to the total of the previously provided reaction component quantities; and (f) providing in said solution the greater of:
  (1) said determined next quantity of step (c), or
  (2) an amount of not less than 0.1 percent of the total of the previously provided quantities of the reaction component.

5. A method as defined in claim 4, wherein the quantity to be provided is an amount of not less than 0.5 percent of the total of the previously provided quantities of said reaction component.

6. A method as defined in claim 4, wherein the quantity to be provided is an amount of not less than 1 percent of the total of the previously provided quantities of the reaction component.

7. A coulometric titration method for determining the content of at least one given component in a chemical solution capable of reacting with at least one reaction component, comprising the steps of:
  (a) successively providing in a chemical solution quantities of at least one reaction component starting with one initial preselected quantity of said at least one reaction component;
  (b) measuring the change of a certain physicochemical value which results from the reaction of each of said reaction component quantities with said one given component;
  (c) determining the next successively provided quantity of said reaction component as a function of said change of said physicochemical value resulting from an immediately preceding provided quantity of said reaction component;
  (d) determining the total of the previously successively provided quantities of said reaction component including said immediately preceding quantity;
  (e) determining said next reaction component quantity as a percentage relative to the total of the previously provided reaction component quantities; and
  (f) providing in said solution the greater of:
    (1) said determined next quantity of step (c), or
    (2) an amount of not less than 0.1 percent of the total of the previously provided quantities of the reaction component.

8. A method as defined in claim 7, wherein said quantity to be provided is an amount not less than 0.5 percent of the total of the previously provided quantities of the reaction component.

9. A method as defined in claim 7, wherein said quantity to be provided is an amount not less than 1 percent of the total of the previously provided quantities of the reaction component.

10. A colorimetric titration method for determining the content of at least one given component in a chemical solution capable of reacting with at least one reaction component, comprising the steps of:
  (a) successively providing in a chemical solution quantities of said at least one reaction component, starting with one initial preselected quantity of said at least one reaction component;
  (b) measuring the change of a certain physicochemical value which results form the reaction of each said reaction component quantity with said one given component;
  (c) determining the next successively provided quantity of said reaction component as a function of said change of said physicochemical value resulting from an immediately preceding provided quantity of said reaction component;
  (d) determining the total of the previously successively provided quantities of said reaction component including said immediately preceding quantity;
  (e) determining said next reaction component quantity as a percentage relative to the total of the previously provided reaction component quantities; and
  (f) providing in said solution the greater of:
  (1) said determined next quantity of step (c), or
  (2) an amount of not less than 0.1 percent of the total of the previously provided quantities of the reaction component.

11. A method as defined in claim 10, wherein said quantity to be provided is an amount of not less than 0.5 percent of the total of the previously provided quantities of the reaction component.

12. A method as defined in claim 10, wherein the quantity to be provided is an amount of not less than 1 percent of the total of the previously provided quantities of the reaction component.

13. A method for the titrimetric determination of the content of at least one given component in a chemical solution capable of reacting with at least one reaction component, comprising the steps of:
  (a) successively providing in a chemical solution quantities of at least one reaction component, starting with one initial preselected quantity of said at least one reaction component;
  (b) measuring the change of a certain physicochemical value which results from a reaction of each said reaction component quantity with said given one component;
  (c) determining the next successively provided quantity of said reaction component as a function of said change of said physicochemical value resulting from an immediately preceding provided quantity of said reaction component;
  (d) determining the total of the previously provided quantities of said reaction component including said immediately preceding quantity.;
  (e) determining said next reaction component quantity as a percentage relative to the total of the previously provided reaction component quantities; and
  (f) providing in said solution the greater of:
    (1) an increment corresponding with said next determined reaction component quantity, of step (c) or
    (2) an increment of not less than 0.1 percent of the total of the previously provided quantities of said reaction component.

* * * * *